United States Patent
Thong

(10) Patent No.: US 6,236,893 B1
(45) Date of Patent: May 22, 2001

(54) SINGLE-ELECTRODE LEAD, IN PARTICULAR FOR IMPLANTABLE DEFIBRILLATORS

(75) Inventor: Tran Thong, Portland, OR (US)

(73) Assignee: Biotronic Mess- und Therapiegeräte GmbH & Co. Ingenieurbüro, Berlin (DE)

( * ) Notice: Subject to any disclaimer, the term of this patent is extended or adjusted under 35 U.S.C. 154(b) by 0 days.

(21) Appl. No.: 09/225,741

(22) Filed: Jan. 6, 1999

(30) Foreign Application Priority Data

Jan. 10, 1998 (DE) ................................ 198 00 697

(51) Int. Cl.$^7$ ....................................... A61N 1/05
(52) U.S. Cl. ............................ 607/123; 607/122
(58) Field of Search ......................... 607/119, 122, 607/123, 4, 5

(56) References Cited

U.S. PATENT DOCUMENTS

| | | | |
|---|---|---|---|
| 4,499,907 | * 2/1985 | Kallok et al. | 607/122 |
| 5,107,834 | 4/1992 | Ideker et al. | |
| 5,456,706 | * 10/1995 | Pless et al. | 607/122 |
| 5,534,022 | * 7/1996 | Hoffmann et al. | 607/122 |
| 5,571,163 | * 11/1996 | Helland | |
| 5,755,762 | * 5/1998 | Bush | |
| 5,913,887 | * 6/1999 | Michel | 607/123 |
| 5,999,853 | * 12/1999 | Stoop et al. | 607/9 |
| 6,076,019 | * 6/2000 | Rutten | 607/123 |

FOREIGN PATENT DOCUMENTS

| | | |
|---|---|---|
| 296 03 805 | 8/1997 | (DE) . |
| 0 661 078 | 7/1995 | (EP) . |

* cited by examiner

*Primary Examiner*—Carl H. Layno
(74) *Attorney, Agent, or Firm*—Browdy and Neimark

(57) ABSTRACT

A single-electrode lead, in particular for implantable defibrillators, is provided with
 a tubular, flexible lead body;
 a ventricular tip electrode;
 a ventricular, in particular helical shock electrode;
 an atrial, in particular helical shock electrode; and
 electric lines guided in the lead body to the individual electrodes.

For improved atrial signal detection, a separate detection electrode is allocated to the atrial shock electrode and is electrically connected thereto such that both electrodes have a joint line.

7 Claims, 1 Drawing Sheet

SINGLE-ELECTRODE LEAD, IN PARTICULAR FOR IMPLANTABLE DEFIBRILLATORS

BACKGROUND OF THE INVENTION

1. Field of the Invention

The invention relates to a single-electrode lead, in particular for implantable cardioverter defibrillators (ICDs) comprising a tubular, flexible lead body; a ventricular tip electrode; a ventricular, in particular helical shock electrode; an atrial, in particular helical shock electrode; and electric lines guided in the lead body to the individual electrodes.

2. Background Art

As regards the background of the invention, implantable defibrillators are customarily equipped with single-electrode leads, which are inserted via the vena cava and the right atrium into the right cardiac ventricle. Defibrillators serve among other things for the treatment of tachycardia conditions in which the heart, beating at a pathologically high frequency, is reset to its normal condition by the delivery of a shock of an electric voltage with amplitudes of some hundreds of volts.

So as to be able to detect the condition of the heart, implantable cardioverter defibrillators have input channels for the signals measured atrially and ventricularly in the heart and treated and amplified electrically in the input channels. These input channels are also utilized for the customary heart pacemaker functions that an ICD normally has. For example, a VDD heart pacemaker comprises the steps of ventricular (=V) stimulation, and atrial and ventricular (D=double) detection of the cardiac signals, the ventricular stimulation taking place only upon demand (=D), i.e. when the heart shows no ventricular self-stimulated action.

Problems are posed by the detection of the electric signal, to be measured, of atrial stimulation, which is designated as P wave in electrocardiography. This signal is comparatively weak and, therefore, hard to detect. Moreover, the signal quality to be measured depends decisively on the properties of the electrodes positioned in the atrium. In the case of single-electrode leads of heart pacemakers and ICDs, either annular or helical electrodes are placed in the atrium, floating in the blood stream without contacting the cardiac wall.

Annular electrodes of heart pacemakers only have few millimeters of length, therefore offering acceptable sensing properties. Shock electrodes of defibrillators must be of large surface design in order for too high local power densities to be prevented from originating in spite of the high electric powers which are emitted upon delivery of a shock. These power densities might damage the myocardium.

It is known that atrial signals (P wave) can be detected by the ventricular and atrial shock electrode. However, a problem resides in that the shock electrodes conventionally have a length exceeding the electric wave front which migrates along the myocardium during the stimulation of the heart. This electric wave front leads to the signal to be detected. In the case of an elongated electrode, the positive and negative amplitudes of the wave front integrate approximately to zero and the signals thus measurable are restricted primarily to weak initial and final amplitudes. These are produced when the wave front reaches or leaves the helical shock electrode.

So as to improve the detection properties, it is conceivable, similarly to the ventricular tip electrode or annular electrode (provided the latter is available) to mount a corresponding additional electrode of comparatively small dimensions in the atrial area of the electrode lead. However, this would result in at least one further electric line being added to the existing at least three lines in the lead body. More and more lines must be provided for further electrodes, which would result in a thicker and, above all, more rigid electrode lead. However, this is not desirable with a view to simplest possible implantability and tolerance of the lead.

SUMMARY OF THE INVENTION

Proceeding from the described prior art problems, it is the object of the invention to develop a single-electrode lead of the generic type in order for the detectability of atrial stimulation signals to be considerably improved.

This object is attained by a detection electrode for the detection of the cardiac atrium stimulation signal which is allocated to the atrial shock electrode and positioned at a distance a therefrom on the lead body, the detection electrode being electrically connected to the atrial shock electrode such that both electrodes have a joint line. In this regard, a detection electrode is allocated to the atrial shock electrode for the detection of the cardiac atrium stimulation signal, the detection electrode however having no electric line of its own, but being electrically connected to the atrial shock electrode. Consequently, both electrodes, namely the detection electrode and the atrial shock electrode, can have a joint line. There is no need to increase the number of lines in the electrode lead. Nevertheless a high signal amplitude is attained by the detection electrode which is much smaller by function than the shock electrode. Details of this will become apparent from the description of the exemplary embodiment.

According to advantageous embodiments of the invention, the electric connection of the detection electrode can be put into practice in a very simple manner by an extension line of the line of the atrial shock electrode. Continuing the helix of the shock electrode is also conceivable.

An advantageous position of the detection electrode has been found to be at a distance of 1 cm to 4 cm from the shock electrode. By advantage, the detection electrode is disposed between the atrial and the ventricular shock electrode.

Details of the invention will become apparent from the ensuing description of a preferred exemplary embodiment of the invention, taken in conjunction with the drawings.

DESCRIPTION OF THE PREFERRED EMBODIMENT

Figure 1:
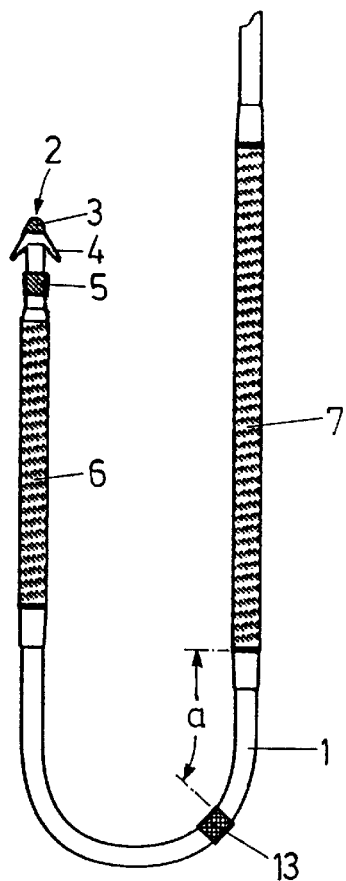
FIG. 1 is a partial lateral view of a single electrode lead for an implantable cardioverter defibrillator.

As seen in FIG. 1, the single electrode lead comprises a tubular, flexible lead body 1 of insulating silicone material. A first ventricular tip electrode 3 is disposed on the tip 2 of this lead body 1 and can be anchored in the myocardium of the ventricle by means of barb-type projections 4 standing out laterally.

A ventricular annular electrode 5 is disposed as a detection electrode approximately 2 cm to 3 cm behind the tip 2 of the lead, cooperating with the tip electrode 3 for bipolar detection of the ventricular stimulation signals of the heart.

The side of the annular electrode 5 turned away from the tip is followed by a first elongated ventricular shock electrode 6 which is coiled from a helical platinum/iridium wire and rests on the lead body 1. The length of the shock electrode amounts for example to 4 cm, the distance from the annular electrode 5 to approximately 1.7 cm.

At a distance from the tip 2 of the lead ranging between 13 cm and 18 cm, provision is made for an atrial shock electrode 7 which again consists of a helically coiled platinum/iridium wire. Atrial positioning of the shock electrode 7 also implies that the electrode tends to be located in the area of the vena cava.

Figure 2:
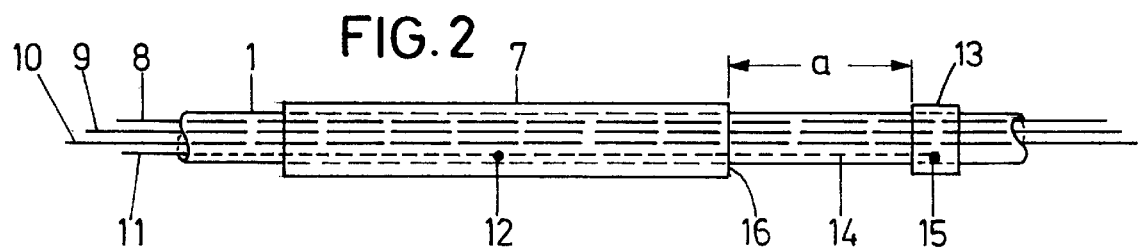
FIG. 2 is a lateral detail view of the electrode lead in the vicinity of the atrial shock electrode with the additional detection electrode.

As roughly outlined in FIG. 2, four lines 8, 9, 10, 11 are provided within the lead body 1, namely for the tip electrode 3, the ventricular annular electrode 5, the ventricular shock electrode 6 and the atrial shock electrode 7. The three lines 8, 9, 10 for the three electrodes mentioned first are illustrated by long dashes in FIG. 2. The line 11 of short dashes serves for the connection of the shock electrode 7, as roughly outlined in FIG. 2 by the connecting point 12.

As further seen in FIGS. 1 and 2, another annular detection electrode 13 is provided between the ventricular and the atrial shock electrode 6, 7, having a length of only a few millimeters as compared to the atrial shock electrode 7 of for example 7 cm of length. In this regard the ratios of dimensions represented in FIGS. 1 and 2 are not true to scale.

The detection electrode 13 is allocated to the atrial shock electrode 7 and electrically connected thereto. To this end, the line 11 possesses an extension line 14 which leads to the detection electrode 13, there being anchored at the wiring point 15. The distance a between the detection electrode 13 and the edge 16 of the atrial shock electrode 7 amounts to approximately 1 to 4 cm.

The advantages in terms of measuring implementation to be attained by the aid of the detection electrode 13 will be explained, taken in conjunction with the diagrammatic electrocardiogram according to FIG. 3. This ECG can be measured completely by the detection electrode 13 and by either the tip electrode 3, the annular electrode 5 or the shock electrode 6.

It is to be assumed that the ventricular stimulation of the heart is to be detected by the aid of the tip electrode 3 and the annular electrode 5. Via a corresponding input channel on the ICD (not shown), the voltage between these two electrodes 3, 5 is detected, prepared and the QRS signal recognizable in the electrocardiogram according to FIG. 3 is generated.

Figure 3:
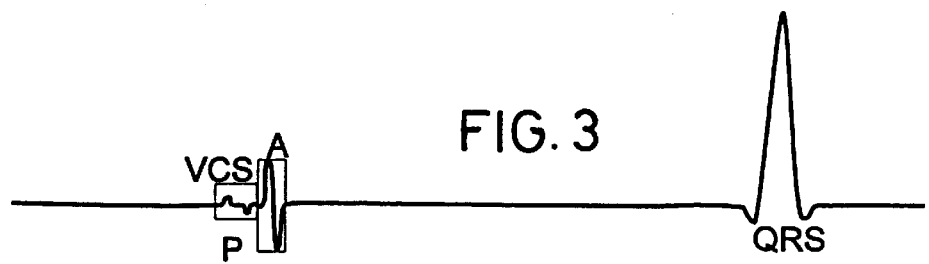
FIG. 3 is a simplified diagrammatic electrocardiogram for the illustration of atrial and ventricular signal detection.

In the electrocardiogram, atrial stimulation manifests itself by the so-called P wave which, in the electrocardiogram according to FIG. 3, is represented by the signal complex preceding the QRS signal. Conventionally, this P wave is detected either by measurement of the voltage between the atrial and the ventricular shock electrode 6, 7 or between the atrial shock electrode 7 and the tip electrode 3. Consequently, the voltage between the line 11 (for the shock electrode 7) and the line 8 (for the tip electrode 3) or the line 10 (for the ventricular shock electrode 6), respectively, is detected and evaluated at the associated ICD input channel.

In the electrocardiogram according to FIG. 3, the atrial stimulation measured via the atrial shock electrode 7 manifests itself by the two chronologically successive and very weak positive and negative amplitudes in the area of the P wave which is enclosed by a solid line and denoted by VCS. As discussed at the outset, the stimulation wave front entering the shock electrode and its leaving same are detected as a measuring signal. Of course, such a signal is rather poor for evaluation purposes.

The additional detection electrode 13 helps obtain a signal of strongly improved quality as opposed to the signal discussed above. This is the signal located in the area A enclosed by a solid line in the electrocardiogram according to FIG. 3. The improved signal quality is primarily due to the fact that the detection electrode, in addition to being small-surfaced, also has a sufficient distance from the shock electrode 7 so that the integrating effect during the propagation of the wave front along the shock electrode 7 is already terminated when the wave front migrates along the detection electrode 13.

Summing up it can be said that a reproduction of the real depolarisation wave front as it occurs in the heart during atrial stimulation is created in the electrocardiogram due to the design of the detection electrode 13 as a narrow ring. Additionally, signal detection can be improved in known manner by the detection electrode 13 being correspondingly coated.

For completion it can be said that an advantage of a great distance of the detection electrode 13 from the atrial shock electrode 7 resides in that the detection electrode 13 can be applied to the atrial heart wall, which generates an even stronger signal as compared to an electrode freely floating in the blood stream.

Finally, attention is drawn to the fact that the retroaction of the QRS complex on the atrial stimulation measuring channel is prevented by a retardation of the atrial channel that is customary in atrial-ventricular detectors and by corresponding scanning of the QRS complex from the measuring channel which is appropriate for detecting the P wave.

What is claimed is:

1. A single-electrode lead, in particular for implantable defibrillators, comprising a tubular, flexible lead body (1);

a ventricular tip electrode (3);

a ventricular shock electrode (6);

a large area atrial shock electrode (7)

electric lines (8, 10, 11) each guided in the lead body (1) to one of the tip electrode (3), the ventricular shock electrode (6) and the atrial shock electrode (7); and a small area detection electrode (13) for detection of a cardiac atrium stimulation signal (P), which detection electrode (13) is allocated to the large area atrial shock electrode (7) and positioned at a distance (a) therefrom on the lead body (1), the detection electrode (13) being directly electrically connected to the atrial shock electrode (7) such that both electrodes (7, 13) have a single common line (11).

2. An electrode lead according to claim 1, wherein the detection electrode (13) is electrically connected via an extension line (14) of the line (11) of the atrial shock electrode (7).

3. An electrode lead according to claim 1, wherein the detection electrode (13) is an annular electrode.

4. An electrode lead according to claim 1, wherein the detection electrode (13) is located at a distance (a) of 1 to 4 cm from an adjacent edge (16) of he shock electrode (7).

5. An electrode lead according to claim 1, wherein the detection electrode (13) is disposed between the two shock electrodes (6, 7).

6. An electrode lead according to claim 1 wherein said detection electrode (13) has a length which is smaller then that of said atrial shock electrode (7).

7. An electrode lead according to claim 6 wherein said detection electrode (13) has a length of a few millimeters.

* * * * *